United States Patent [19]

Bresnahan et al.

[11] 4,041,609

[45] Aug. 16, 1977

[54] FOOT CONTROL FOR DENTAL EQUIPMENT

[75] Inventors: Robert A. Bresnahan, York, Pa.; Edward W. Bass, Claymont, Del.; William G. Mader, York, Pa.

[73] Assignee: Dentsply Research & Development Corporation, Milford, Del.

[21] Appl. No.: 688,863

[22] Filed: May 21, 1976

[51] Int. Cl.² .......................................... A61C 19/02
[52] U.S. Cl. .......................................................... 32/22
[58] Field of Search ................. 32/22, DIG. 3, 27, 28; 251/295; 74/99, 100

[56] References Cited

U.S. PATENT DOCUMENTS

| | | | |
|---|---|---|---|
| 1,836,766 | 12/1931 | Mullet et al. | 92/168 |
| 2,498,699 | 2/1950 | Mullet et al. | 4/167 |
| 2,981,915 | 4/1961 | Sonstegard | 32/22 |
| 3,039,193 | 6/1962 | Williams | 32/28 |
| 3,054,187 | 9/1962 | Staunt | 32/27 |
| 3,296,698 | 1/1967 | Staunt | 32/28 |
| 3,471,928 | 10/1969 | Billin | 32/22 |
| 3,596,102 | 7/1971 | Brooks | 250/215 |

Primary Examiner—Robert Peshock
Attorney, Agent, or Firm—C. Hercus Just; Jerry W. Berkstresser

[57] ABSTRACT

A foot control for a dental unit having a control unit for the delivery of power to operate dental equipment, and including a plunger to effect a range of speeds for the equipment, said control unit being operated by an actuating member which engages said plunger to depress it, and said actuating member being universally actuated by a pedal selected from a series thereof arranged in spaced relationship upon a base and extending radially from the base and capable of being moved either pivotally in a horizontal plane or depressed vertically downward to actuate said actuating member in one direction to depress the plunger of said control unit to a degree corresponding to the speed desired for the dental equipment.

16 Claims, 12 Drawing Figures

FOOT CONTROL FOR DENTAL EQUIPMENT

BACKGROUND OF THE INVENTION

Before the advent of dental handpieces driven by air turines at high speeds, the handpieces then used by the dental profession were driven by belts that were energized by an electric motor, the belts extending around pulleys connected to a series of articulated arms, and the dental handpiece was connected to the outer end of the outermost arm and employed a pulley on the outer end of the handpiece which was driven by one of the belts referred to above. Normal speeds for such handpieces range somewhere in the vicinity of 8,000 to 10,000 r.p.m. Modern, high speed handpieces driven by air turbines operate at speeds between 300,000 and 400,000 r.p.m. or higher and dental burs driven at these speeds are far less painful to the patient than the burs driven by the previous slow speed handpieces.

Belt driven handpieces operated at variable speeds by means of controlling the speed of the electric motor through the use of a foot control which primarily comprised a rheostat operated by a pedal extending radially from the foot control and pivoted about a vertical axis. Possibly somewhat resulting from perpetuation of a habit, it has been generally customary to provide control units for such high speed handpieces which employ either a pedal or other means which were movable laterally substantially within a horizontal plane for purposes of varying the speeds of the handpieces. Also, depending upon the posture of a dentist when operating upon a patient, it has been found to be more convenient to operate the foot control by depressing an operating element on the foot control, such as a pedal, annular plate capable of being depressed, or otherwise, whereas in other postures of the dentist, it is more convenient to operate a laterally movable actuating member on the foot control which moves substantially within a horizontal plane.

In view of the foregoing, there is a tendency to provide modern dental foot control units with a plurality of different types of actuating members respectively movably, selectively, in a horizontal plane or a vertical plane. One example of a foot control unit of this type is the subject matter of U.S. Pat. No. 3,471,928, in the name of A. G. Billin, dated Oct. 14, 1969. In this unit, an annular foot-engageable member is adapted to be either depressed or rotated, horizontally, limited distances about the vertical axis of the unit by means of said member being frictionally engaged by the shoe of the dentist. One of the virtues of this control unit is that it can be operated at any location through the full 360° circumference of the annular member.

Not only does the aforementioned patent permit substantially 360° operation of the foot control but, in addition, U.S. Pat. No. 3,596,102, in the name of Gregory W. Brooks, issued July 27, 1971 has an upper, foot-engageable circular member in the form of a relatively flat convex configuration which is intended to be engaged on its upper surface by the foot of a dentist who rotates the member about a central axis of the foot control unit and thereby operates electrical switch mechanism that controls the operation of dental equipment such as handpieces. Only rotary movement of the actuating member is illustrated in said patent and no provision is made for depressing any portion of the perimeter of the circular operation member to actuate the control mechanism.

There also is an earlier U.S. Pat. No. 2,981,915, in the name of R. L. Sonstegard, issued Apr. 25, 1961, which includes a peripheral ring around the lower portion of a circular foot control which is adapted to be pressed radially inward by engagement by the foot of a dentist, for example, for purposes of actuating lever members that operate linkages supporting the movable member of a rheostat to effect variable electrical drive for a dental chair, drill, drill press, or the like. No provision is made for depressing said actuating ring and only inward radial movement is contemplated for actuating the rheostat.

The aforementioned patents illustrate the basic principle of the current types of dental foot control units for dental instruments and especially hanpieces are adapted to be operated from substantially any location around the full 360° of the perimeter of the foot control unit. In view of this tendency and trend, the present invention also is adapted to be operated from substantially any major segment of a full 360° perimeter operation of a foot control unit, while also providing certain improvements to render the unit rugged and capable of long life as well as insuring desired convenience and operation by employment of structural features not found in the prior art, without sacrificing any of the advantages of the prior art. Details of such improved structure are set forth below.

SUMMARY OF THE INVENTION

It is the principal object of the present invention to provide a foot control unit adapted particularly to control the delivery of fluids and especially gaseous fluids under pressure to dental instruments, especially dental handpieces, to control the operation thereof at variable speeds, said device employing a plurality of foot-engageable pedals which extend radially from the central axis of the foot control unit and are capable of selectively of being either depressed or moved pivotally and laterally within a horizontal plane, either of which movements operate the control element to the desired degree in order to produce a desired speed of operation of the dental instrument.

It is another object of the invention to include an actuating member in the foot control unit in the form of a spider provided with radially extending arms spaced equal distances apart, said actuating member being directly engageable with the plunger of a control unit for the supply of fluid to the dental instrument, one of said arms being adapted to be depressed by operation of a selected pedal regardless of whether the pedal is moved pivotally in a horizontal plane or depressed vertically, the remaining arms serving as fulcrums to effect such depression of the plunger of the control unit.

A still further object of the invention is to interconnect the aforementioned pedal with the respective arms of the actuating spider by means of links which are connected for universal movement at one end to one of the pedals and the opposite end has a transverse, flat head thereon which is adapted to be rocked between a fixed surface and a surface of one of said arms of the actuating spider in order to effect a depression of said arm when the pedal is pivotally moved in a horizontal direction, while said head also is arranged to engage an arm of said spider when the pedal for that particular arm is depressed as distinguished from being moved pivotally in a horizontal direction.

It is still another object of the invention to provide various details of construction which render the foot control unit rugged and long lasting, fool-proof in operation, as well as insurance against mal-functioning of the various elements of the foot control unit. In said foot control unit, the control unit for operating fluids and especially gaseous fluids under pressure is a pressure regulator valve in nature and the actuating plunger is preferably movable in a vertical direction downward when operated by said actuating spider member, the degree of downward movement determining the speed of operation of the dental instrument such as the handpiece, between rest condition and maximum speed.

Details of the foregoing objects and of the invention, as well as other objects thereof, are set forth in the following specification and illustrated in the accompanying drawings comprising a part thereof.

DETAILED DESCRIPTION

Figure 1:
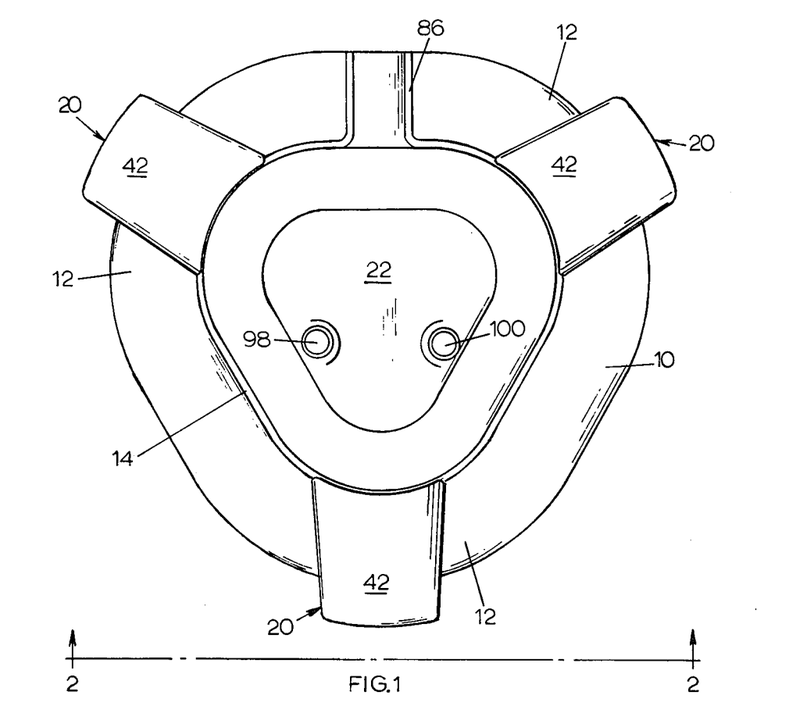
FIG. 1 is a top plan view of the foot control unit embodying the principles of the present invention, said view illustrating the plurality of radially extending foot pedals which are equally spaced apart around the vertical axis of the unit.
Figure 2:
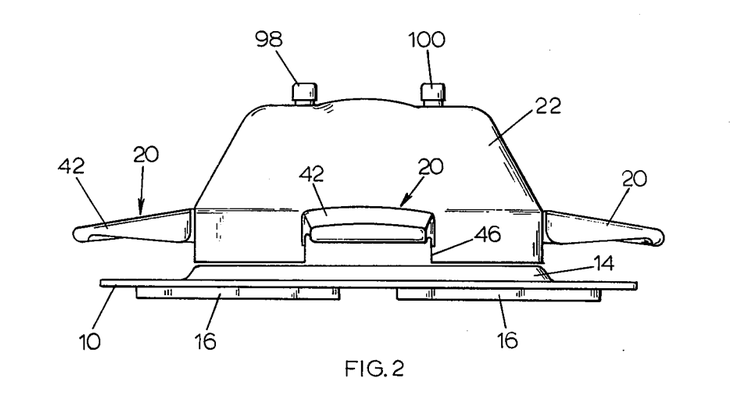
FIG. 2 is a side elevation of the foot control unit shown in FIG. 1 as seen from the line 2—2 of FIG. 1.
Figure 3:
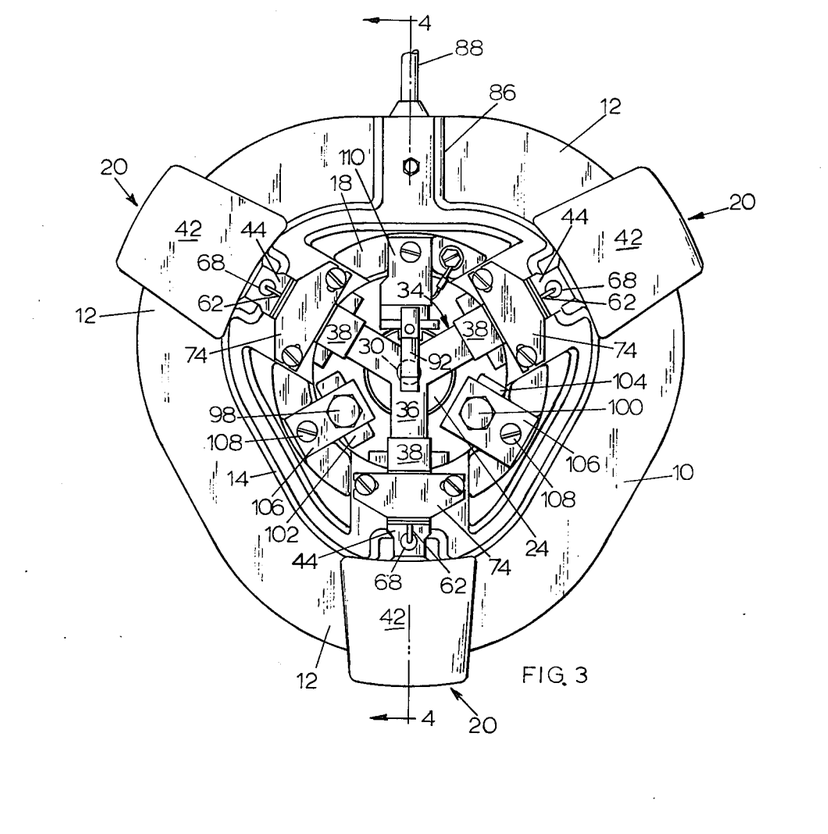
FIG. 3 is a view similar to FIG. 1 but in which the cover for the central portion of the control unit has been removed to expose details of the actuating mechanism enclosed within said cover.

Referring to FIGS. 1-4, the foot control unit illustrated therein, which embodies the principles and details of the present invention, comprises a base 10 which preferably is formed from a sheet of synthetic resin of any suitable type that is relatively stiff and of suitable thickness, such as of the order of ⅛ inch. In plan view, as shown in FIG. 1 and 3, base 10 is somewhat triangular in shape with widely curved corners 12, whereby the base is nearly circular in configuration. The central portion 14 of the base 10 is offset upwardly from the plane of the rim portion of base 10 to provide clearance in the undersurface of said base to accommodate screws and other attaching means, some of which are visible in FIG. 4. Also, the base 10, on its lower surface, is provided with the plurality of cushioning pads 16 which preferably are of a somewhat frictional nature to maintain the control unit in a desired location upon a supporting surface such as a floor in a dental operatory.

Figure 11:
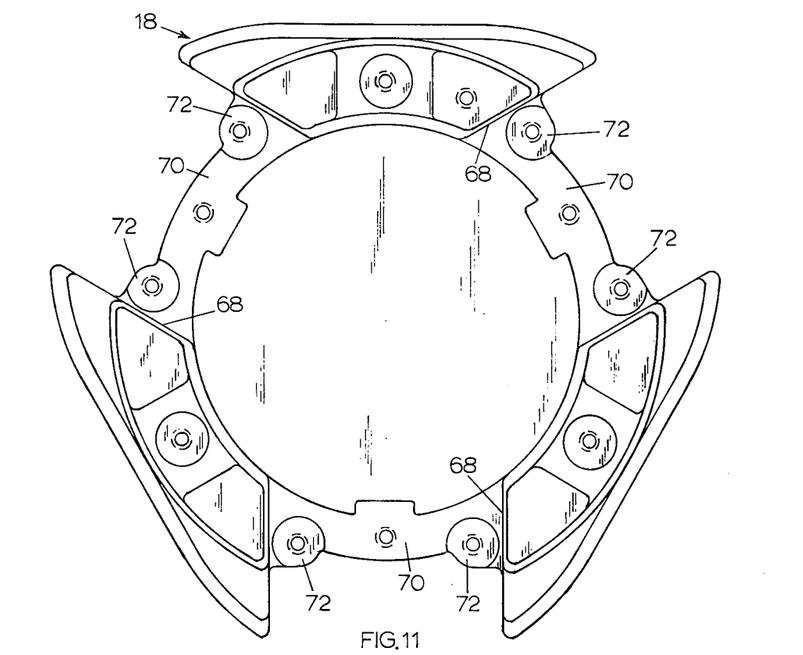
FIG. 11 is a top plan view of a heavy body member incorporated in the foot control unit and supported from the upper surface of a plate-like base member, said views illustrating certain spaces to receive and support various fixed and movable elements comprising the operating mechanism of the foot control unit shown in the preceding Figures.
Figure 12:
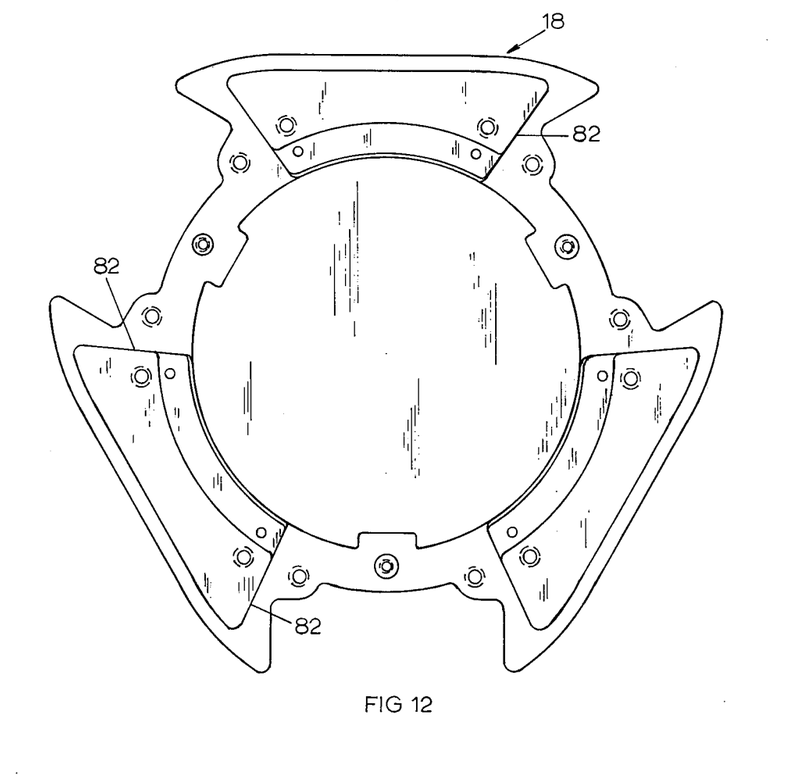
FIG. 12 is a bottom plan view of the heavy body member shown in FIG. 11 and illustrating additional spaces to receive and/or support various structural details of the foot control unit illustrated in the preceding Figures.

Secured to the upper surface of the central portion 14 of base 10 is a heavy body member 18, details of which are best illustrated in FIGS. 11 and 12 which, respectively, are top and bottom plan views thereof. Body member 18 has several purposes, one of which is to provide suitable weight which serves to maintain the entire foot control unit at a desired location upon the floor of a dental operatory, for example, particularly for purposes of permitting the pivotal movement of any of the pedals 20 about the pivots at the inner ends thereof and within a horizontal plane. The second purpose of the body member 18 is to provide support means for various elements of the foot control unit, described in detail hereinafter.

The central portion of the foot control units supports a molded, removable cover 22 which encloses all of the working elements of the control unit with exception of the pedals 20 which project radially from said cover, which is of an esthetic nature.

Figure 4:
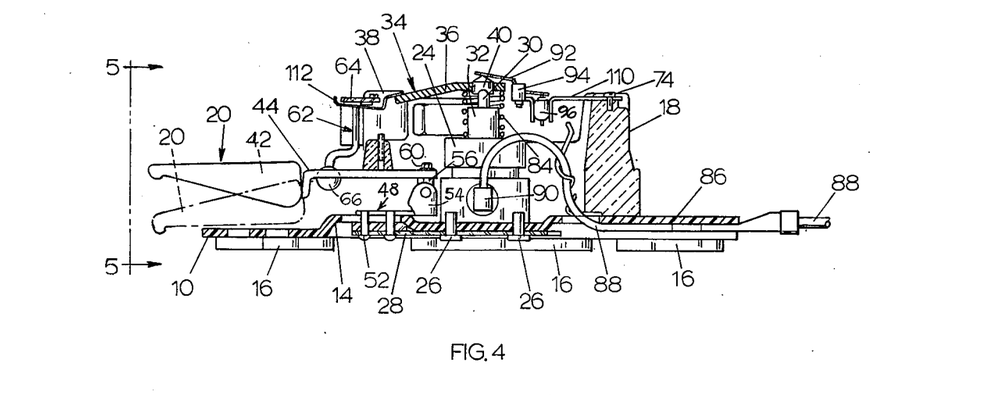
FIG. 4 is a vertical sectional elevation of the foot control unit of the invention arranged as in FIG. 3 with the cover removed and illustrating details shown along the line 4—4 of FIG. 3.

Mounted preferably centrally upon the base 10 is a control unit 24, the lower portion of which is securely fastened to the central portion 14 of base 10 by a plurality of screws 26 which are best shown in FIG. 4. Said screws also pass through a triangular metal plate 28 which underlies the central portion of base 10, as also shown in FIG. 4, for purposes of providing rigidity for certain elements described in detail hereinafter. The control unit 24 may, essentially, by any one of a number of different types of control units. In one type of foot control unit embodying the present invention, the control unit 24 comprises a pressure regulator valve for controlling the delivery of air, under pressure, from a source thereof to selected dental instruments such as dental handpieces of the air-turbine type. However, the control unit 24, in other applications of foot control units may comprise electric switch means or a combination of pressure regulator valve and electric switch means, as required for certain dental equipment to be controlled by the overall foot control unit. For purposes of the present invention, therefore, the essential characteristic of the control unit 24 is that it have a vertically movable plunger 30 which projects upwardly through a bearing boss 32, which is also best shown in FIG. 4, whereby the principle function of all of the operating mechanism of the foot control comprising the present invention is to depress the plunger 30 for purposes of operating the control unit 24 in a manner to control the operation of selected dental equipment, not shown, such as dental handpieces or otherwise.

Figure 8:
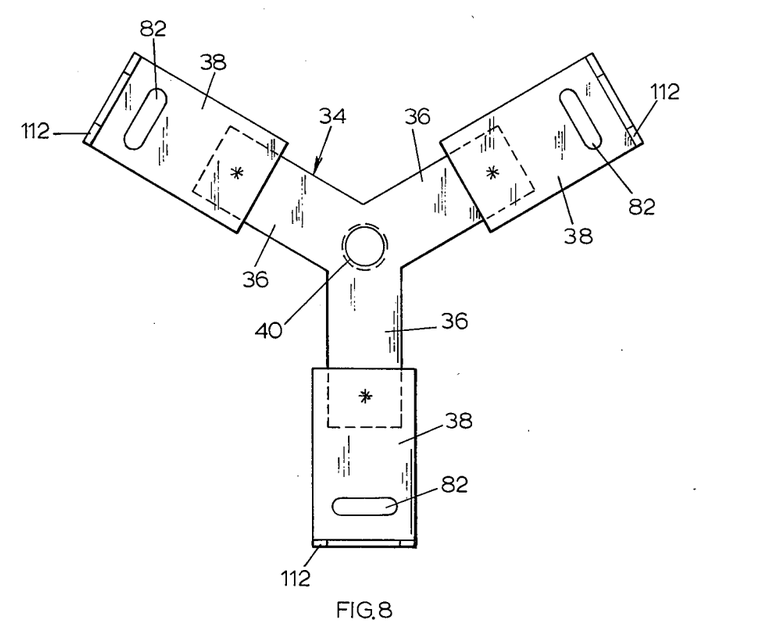
FIG. 8 is a top plan view of the actuating spider member embodied in the foot control unit illustrated in the preceding views.

Plunger 30 is depressed by means of an actuating member 34 which preferably is in the form of a spider that has three arms 36, see FIG. 8, all of which subtend equal angles therebetween, as is clearly illustrated in FIG. 8. Connected fixedly to the outer ends of each of the arms 36 of actuating member 34 are extension members 38, the function of which is set forth below. Mounted centrally of actuating member 34 and threadably extending there through is a cap member 40, the upper end of which preferably is in the shape of a short cone as can best be seen in FIG. 4. The threaded arrangement permits initial adjustment of the member 40 with respect to the actuating member 34 and when that adjustment has been achieved incident to completing the manufacture and testing of the foot control unit, suitable sealing material, such as epoxy cement or otherwise is applied to the cap member and actuating member 34 to prevent at least accidental movement of the cap member from its adjusting position. The lower surface of cap member 40 also preferably is provided with a recess which receives the preferably rounded upper end of plunger 30, as can be seen in FIG. 4 and thereby maintain the relative positioning of the actuating member 34 with respect to the plunger 30.

Pedals 20 are preferably of a composite nature and each includes a foot-engageable shoe 42 which is formed from any suitable moldable material, preferably synthetic resin, and includes downwardly extending side members of appreciable width, as best shown in FIGS. 2 and 4, in order that said side members may be engaged by the side of the shoe of a dentist when it is desired to move the pedals 20 of laterally, within a horizontal plane, to effect actuation of the plunger 30 of control unit 24. Each shoe 42 is connected to the outer end of a pedal support member 44, the mid portion of which projects through a notch 46 formed in the lower rim of cover 22, as seen in FIG. 2. The pedal support members 44 extend radially from the axis of control unit 24 and the inner ends thereof are connected for universal movement with respect to hinge members 48 which are shown best in FIGS. 4 and 6. The hinge members 48 have a flat leaf 50 which is secured by screws 52 fixedly to the central portion 14 of base 10, see FIG. 4. The inner end of leaf 50 is provided with a pair of transversely spaced ears 54 between which one end of a hinge pivot 56 is positioned for movement by a transverse pin 58. The inner end of pedal support member 44 is pivotally connected to the hinge pivot 56 by a screw 60 in a manner which permits limited pivotal movement of the pedal support member 44 about the axis of the screw 60 with respect to hinge pivot 56.

From the foregoing, it will be seen that the pedal support members 44 are mounted at the inner ends thereof for limited universal movement relative to both horizontal and vertical pivotal axes. The reason for this is to provide one of the principle virtues of the present invention, namely, that the provision of three pedals 20 at evenly spaced positions around the circumference of the base 10 is to always have one of the pedals in position for ready engagement by the dentist, for example, regardless of where he is standing or sitting in the vicinity of the foot control unit. Also, the dentist can actuate the control unit 24 by depressing the plunger 30 thereof through the operation of the pedal 20 most conveniently located for engagement by the foot of the dentist and the pedal which is to be engaged by the dentist is capable of depressing the plunger 30 regardless of whether the pedal 20 is moved in a horizontal plane about its pivot 60 or is depressed vertically downward and thereby move the support member 44 about the horizontal axis of pin 58 which extends through the ears 54 of each hinge member 48. Therefore it will be seen that such selective operation of the pedals 20 is made possible by the limited universal pivotal movement of the pedal support members 44 relative to the hinge members 48.

Figure 9:
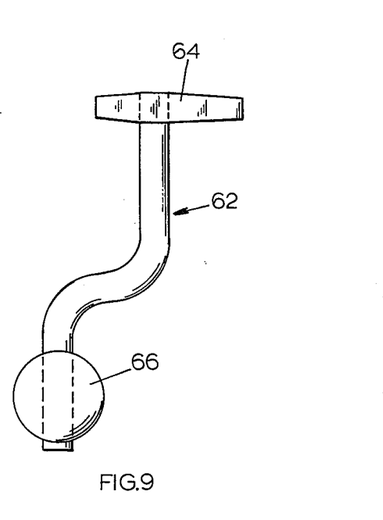
FIG. 9 is a side elevation of one of the links which extends between the spider shown in FIG. 8 and one of the pedals in the manner illustrated in FIG. 6.
Figure 10:
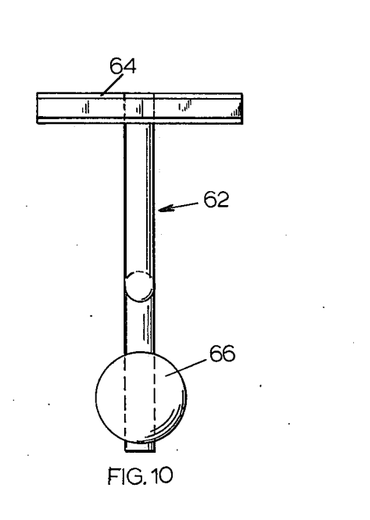
FIG. 10 is a view of the link shown in FIG. 9 as seen from the right-hand side thereof in FIG. 9.

Such selective lateral movement of the pedals 20 or downward depression thereof is transmitted to the actuating member 34 by the use of connecting members 62 which are of a special shape as can readily be appreciated from FIGS. 9 and 10. Fixed to the upper ends of each of the connecting members 62 is a flat, transverse head 64 and connected to the lower end of the lower offset portion of the member 62 is a metal ball 66 which has a slightly larger diameter than a circular hole 68 which is formed in each pedal support member 44 intermediately of the ends thereof, thereby providing a substantially universal connection between each pedal support member 44 and its respective connecting member 62.

Figure 5:
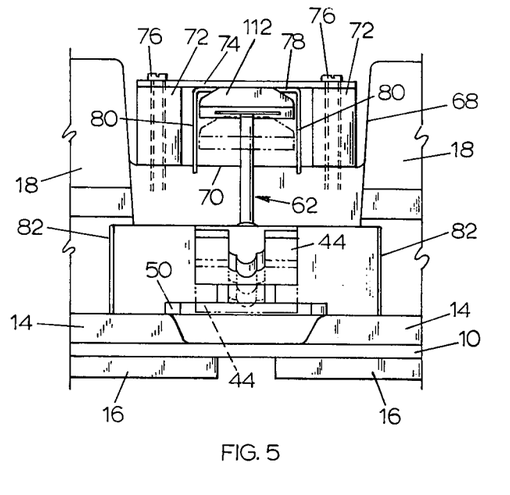
FIG. 5 is a fragmentary vertical end view of one of the pedals of the foot control unit and the mechanism operated thereby as seen from the line 5—5 of FIG. 4.
Figure 6:
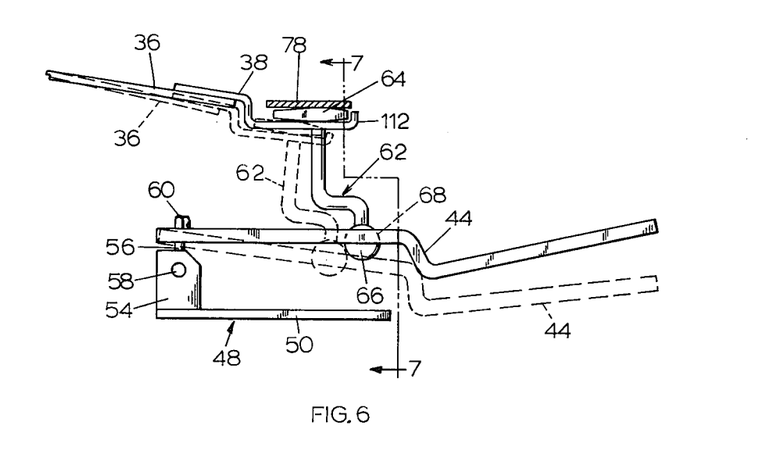
FIG. 6 is a fragmentary vertical elevation, partly in section, illustrating in full lines one position of a selected operating pedal and the mechanism moved thereby, and in phantom, showing the relative position of the elements when the pedal is depressed.

From FIG. 5, which is an enlarged, fragmentary view of the mechanism shown in FIG. 6, as seen from the right-hand end of FIG. 6 looking toward the left-hand end, it'll be seen that the heavy body member 18 is provided with notches 68 having a bottom 70 and a pair of posts 72, see FIG. 5, extend upward from the bottom 70 of the notches 68 a limited extent for purposes of supporting a bridge plate 74 which extends between the posts that are secured thereto by screws 76. Connected to the lower surface of each of the bridge members 74 is a U-shaped bracket for retaining members 78, the legs 80 of which extend downwardly closely adjacent the opposite side edges of extension members 38. Extension members 38 are provided with transverse slots 82, see FIG. 8, through which the upper end of connecting members 62 extend so as to dispose the transverse heads 64 on member 62 between the central portions of retaining members 78 and the extension members 38 on arms 36 of the actuating member 34.

Figure 7:
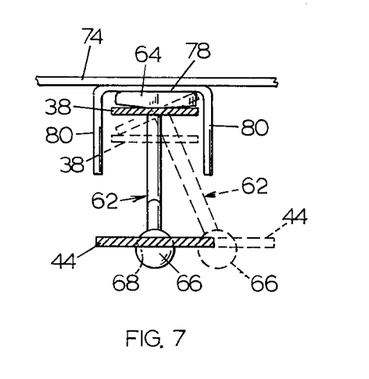
FIG. 7 is a fragmentary vertical elevation of the mechanism shown in FIG. 6, partly in section, in showing the same along the lines 7—7 of FIG. 6.

In FIG. 5, it'll be seen that the heavy body member 18 also is provided with additional notches 82 which extend upward from the lower surface thereof and are vertically aligned with the upper notches 68 in body member 18. This is for purposes of accommodating the pedal support members 44 to permit limited vertical and lateral, horizontal movement of the pedal support members 44 within said notches in order to depress a selected arm 36 of the actuating member 34 and thereby depress the plunger 30 of control unit 24. This is accomplished, selectively, either by vertically depressing a selected foot-engageable shoe 42 downwardly, in which event the connecting member 62 will directly move the extension member 38 of one of the arms 36 of actuating member 34 downwardly due to engagement of transverse head 64 therewith, or one side of the selected shoe 42 may be engaged by the side of the shoe of a dentist and moved laterally, within a horizontal plane, in order to tilt the connecting member 62, as illustrated diagrammatically in phantom, in FIG. 7, which operates to cock the transverse head 64 of the connecting member 62 in a manner which cams the extension member 38 downwardly, as also shown in phantom in FIG. 7 and thereby serves to depress the arm 36 to which extension 38 is connected and thus depress said arm 36 sufficiently to also depress plunger 30 of control unit 24. As can be visualized from FIG. 3, when one of the pedals 20 is depressed or moved laterally, as desired, for purposes of depressing the plunger 30 of control unit 24, the remaining two arms 36 and their extension members 38 remain in engagement with the bridge plates 74 and thus serve as stationary fulcrums for the actuating member 34 which functions as a lever of the second class. Following the completion of the actuation of the control unit 24 and upon the pedal 20 being released by the operator, the plunger 30 of control unit 24 normally is spring pressed outwardly to restore the plunger to its idle position. However, to insure the restoration of the actuating member 34 to its idle position, it'll be seen from FIG. 4, that a coiled spring 84 surrounds the bearing boss 32 and is expansible between the upper end of the main body of control unit 24 and the lower surface of the central portion of actuating member 34.

For purposes of introducing either air under pressure or other fluids, as well as electric conduit mean in the event the control unit 24 comprises an electric switch, it will be seen from FIGS. 1, 3 and 4, that the base 10 is provided with a radially extending raised portion 86 through which either a tubular or electrical conduit 88 extend from a source to a coupling element 90 on the main body portion of control unit 24, see FIG. 4.

Additional features are also included in the specific illustration of the foot control unit comprising the present invention, these primarily being operated by the cap member 40, as shown in FIG. 4. Referring to said FIG. it'll be seen that a loosely pivoted lever 92 is supported intermediately of its ends by a pivot member 94. One end of the lever 92 engages the conical tip of the cap member 40, and the opposite end engages a Microswitch 96 which, for example, is connected in the circuit, not shown, to a solenoid-controlled air valve, the solenoid, for example, being in the same circuit as an auxiliary switch which is actuated, for example, when a dental instrument such as a handpiece is removed from its supports arm or otherwise. Under such circumstances, the removal of the handpiece from its supporting member partially establishes a circuit which is completed when, for example, one of the pedals 20 is actuated to operate the control unit 24 and, incidentally, close the Micro-switch 96 to complete the circuit to said aforementioned solenoid.

In addition, it is popular to include in foot control units of the type to which the present invention pertains, additional control means which, for example, respectively are connected in conduits which respectively furnish water and/or chip-blowing air to a dental handpiece or, further, to provide water or air to some other type of dental instrument such as a syringe. Referring to FIGS. 2 and 3, it will be seen that the present invention provides such supplemental or auxiliary control means referred to above in the form of two foot-engageable plungers 98 and 100 which project through appropriate openings in the cover 22. For example, the plunger 98, when depressed, closes a switch 102, see FIG. 3, which is interconnected to a solenoid, not shown, that operates an air-flow control valve, not shown, established in an air conduit extending between the source of compressed air and a dental instrument. Similarly, plunger 100 operates a switch 104, shown in FIG. 3, which is connected in a circuit, not shown, to a solenoid which controls a flow-control valve in a water conduit line, not shown, extending between a source of water under pressure and a dental instrument. The plungers 98 and 100 and the switches 102 and 104 to which they are respectively connected are supported by simple brackets 106 detachably fixed to the upper surface of body member 18 by screws 108. Similarly, the Micro-switch 96 is affixed to the upper surface of body member 18 by another bracket 110 shown in FIGS. 3 and 4.

From the foregoing, it'll be seen that by utilizing connecting member 62 of the particular shape illustrated especially in FIGS. 6, 7, 9 and 10, and employing the tiltable transverse heads 64 on the upper ends thereof and the metal balls 66 on the lower ends thereof to provide limited universal connection to the pedal support members 44, an operator may select whether or not the pedals 20 are to be depressed at the outer end thereof or moved arcuately about the pivots of the support members 44, within a horizontal plane, for purposes of depressing the plunger 30 of control unit 24 in either event. As described above, the flanges or legs 80 of the retaining member 78 which is stationed stationarily affixed to the bridge plate 74 with respect to each pedal prevents displacement of the transverse head 64 on each connecting member 62 to any appreciable extent in one direction, and it'll be seen particularly from FIG. 6 that the outer end of each extension member 38 is bent upwardly to provide a short vertical flange 112, see FIGS. 5 and 6, which serves to prevent the transverse head 64 from skewing with respect to the vertical axis of connecting member 62 and the slot 82, through which the upper end of each of the connecting members 62 extends, serves to positively prevent movement of the transverse head 64 in a radial direction which is transverse to the movement prevented by the legs 80 of the retaining member 78. Accordingly, any mal-functioning of the movement of the connecting members 72 is prevented even though the transverse heads 64 operate in a somewhat floating manner when the pedals are moved about the pivots on the inner ends thereof within a horizontal plane that results in cocking of the connecting member 62 as well as the transverse heads 64 for purposes of depressing the plunger 30 of control unit 24. The length of the transverse head 64, as viewed in FIG. 10. is fully adequate to effect the desired amount of lowering of the arms 36 and extension members 38 thereon which such cocking of the transverse heads 64 occurs.

The cover 22 is retained in operative position to enclose the operating mechanism shown in detail, for example, in FIGS. 3 and 4 in particular, by either frictionally engaging the periphery of the lower portion of body member 18 or providing some sort of conventional snap-fastening means of simple type.

From the foregoing, it'll be seen that the present invention provides a durable and foolproof foot control unit employing a plurality of radially extending pedals at convenient locations about the periphery of the base of the unit for ample convenience of an operator such as a dentist, whereby the dentist will find one of the pedals quite conveniently located for being operated by either depressing the same or moving it laterally within a horizontal plane, in order to effect actuation of the control unit 24. The design of the exposed portions of the foot control unit is such as to be esthetic as well as utilitarian and the weight of the entire foot control unit is such as to maintain the same by gravity in a desired location upon a supporting surface such as the floor. The static inertia thus provided being fully adequate to permit pivotal movement of the radially projecting pedals without disturbing the position of the base of the foot control unit upon the floor surface supporting the same.

The foregoing description illustrates preferred embodiments of my invention. However, the concepts employed may, based upon such description, be employed in other embodiments without departing from the scope of the invention. Accordingly, the following claims are intended to protect the invention broadly, as well as in the specific forms shown herein.

We claim:

1. A foot control unit for fluids delivered to dental instruments comprising in combination,
    a. a base adapted to be supported upon a surface such as a floor,
    b. a control unit supported upon said base and including a plunger projecting therefrom and adapted to be moved axially in one direction to effect delivery of fluids to a dental instrument,
    c. an actuating member supported above the upper end of said plunger of said control unit,
    d. a plurality of foot-engageable members movably supported by said base at circumferentially spaced locations for movement selectively in horizontal and vertical directions,
    e. connecting members respectively extending between said foot-engageable members and said actuating member, and
    f. depressing means on said connecting members operable to move said actuating member in a direction to move said plunger in said one direction when said foot-engageable members are moved in either said horizontal or vertical directions 2. The foot control unit according to claim 1 in which said foot-engageable members comprise pedals pivotally connected at one end to said base and extending radially outward therefrom for universal movement of the outer ends of said pedals selectively in vertical and horizontal directions.

3. The foot control unit according to claim 2 in which said connecting members are connected at one end to said pedals intermediately of the ends thereof.

4. The foot control unit according to claim 2 in which said pedals extend substantially radially relative to the axis of said plunger of said control unit and said control unit being affixed to said base substantially centrally thereof.

5. The foot control unit according to claim 1 in which said plunger of said control unit is vertical and the said actuating member is positioned coaxially therewith.

6. The foot control unit according to claim 5 in which said actuating member comprises a spider having radial arms equal in number with said foot-engageable members and said arms being movably connected to said connecting members.

7. The foot control unit according to claim 6 further including abutment means fixed relative to said base above the outer end of said spider arm, and said connecting members having transverse heads on the upper ends thereof positioned between said abutment means and the outer ends of said arm, said transverse heads being selectively rockable between said abutment means and outer ends of said arm or depressed by action of said foot-engageable members to depress the center of said actuating member and thereby effect movement of said plunger of said control unit in said one direction.

8. The foot control unit according to claim 7 in which the arms of said spider which are not actuated by a selected pedal are positioned and arranged to serve as fulcrums engageable with said abutment means.

9. The foot control unit according to claim 7 further including retaining means on said abutment means positioned to restrain abnormal horizontal movement of said transverse heads of said connecting members during operation thereof.

10. The foot control unit according to claim 9 in which said retaining means comprise vertical flanges depending from said abutment means.

11. The foot control unit according to claim 1 in which said base is plate-like, said actuating member is a spider having radial arms, and said foot-engageable members are pedals extending radially from the central axis of said foot control unit, said foot control unit further including a heavy body member forming a substantially annular wall supported upon the upper surface of said base, said wall having a plurality of openings evenly spaced around the circumference thereof respectively to receive said radial arms of said spider therethrough.

12. The foot control unit according to claim 11 further including bridge members extending across said openings which receive the arms of said spider, said bridge members forming abutment means engaged by the upper ends of said connecting means.

13. The foot control unit according to claim 12 in which said connecting means comprise links having cross-members fixed to the upper ends thereof and swivel connector means on the lower ends thereof, said cross-members being positioned between said bridge members and the ends of said radial arms and operable to effect lowering of a selected arm when a pedal is depressed or cocking said cross-members between said bridges and the ends of said radial arms when the outer end of one pedal is moved laterally within a horizontal plane to effect such lowering of said selected arm.

14. The foot control unit according to claim 13 in which said swivel connector on the lower end of each connecting link is at least partly spherical and said pedals having holes extending therethrough intermediately of the ends thereof, said holes being of less diameter than the largest diameter of the spherical ends of said links, thereby providing substantially universal type swivel connection between said connecting means and said pedals.

15. The foot control unit according to claim 14 in which said pedals extend radially substantially from the central vertical axis of said foot control unit, one end of each of said pedals extending outwardly beyond said body member and the inner ends of said pedals being connected by swivel units to said base for pivotal movement of said pedals respectively in vertical and horizontal planes.

16. The foot control unit according to claim 1 in which said control unit from which said plunger projects comprises a pressure regulator valve for air under pressure to be delivered to a dental instrument, and said foot control unit further including air inlet and delivery conduits connected to inlet and discharge ports of said regulator valve, said plunger of said control unit being movable through a range of positions respectively to vary the pressure of air delivered by said control unit, said actuating member engaging the upper end of said plunger to depress the same an amount corresponding to a desired air pressure to be delivered to a selected dental instrument, and said foot-engageable members comprising radially extended pedals operable selectively in horizontal and vertical directions to depress said actuating member against said plunger to effect delivery of air to a dental instrument at said desired pressure.

* * * * *